United States Patent [19]

Vollmer

[11] 4,022,852
[45] May 10, 1977

[54] PROCESS FOR MAKING PHOSPHORUS SULFAMIDES

[75] Inventor: Hartfrid Vollmer, Erftstadt Liblar, Germany

[73] Assignee: Hoechst Aktiengesellschaft, Frankfurt am Main, Germany

[22] Filed: July 1, 1975

[21] Appl. No.: 592,255

[30] Foreign Application Priority Data

July 5, 1974 Germany .......................... 2432271

[52] U.S. Cl. .............................. 260/970; 260/932; 260/944; 260/45.7 P
[51] Int. Cl.² .......................................... C07F 9/40
[58] Field of Search .................. 260/932, 944, 970

[56] References Cited

UNITED STATES PATENTS 3,920,733  11/1975  Biram ........................... 260/932 X Primary Examiner—Anton H. Sutto
Attorney, Agent, or Firm—Connolly and Hutz

[57] ABSTRACT

Production of phosphorus-containing sulfamide derivatives of the general formula:

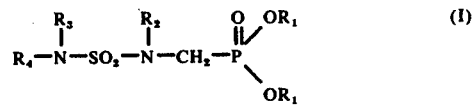

In the above formula, $R_1$ stands for an alkyl radical or a halogen-substituted, alkyl radical having from 1 to 6 carbon atoms or stands for an aryl radical, and $R_2$, $R_3$ and $R_4$, being identical or different, each stand for a hydrogen atom, a hydroxyalkyl group or a radical of the formula:

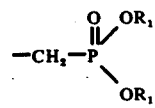

10 Claims, No Drawings

PROCESS FOR MAKING PHOSPHORUS SULFAMIDES

The present invention relates to novel phosphorus-containing sulfamide derivatives of the general formula indicated hereinafter, and to a process for making them.

As disclosed in German published specification Offenlegungsschrift No. 2,315,493, Example 1, it is known that N-dimethylphosphonomethyl-p-toluene sulfamide can be made by reacting toluene sulfonamide with paraformaldehyde in the presence of methanol and sodium methylate to give N-hydroxymethyl-p-toluene sulfonamide and by condensing this latter compound with trimethyl phosphite under dehydrating conditions. Compounds of the N-dimethylphosphonomethyl-p-toluene sulfamide series are suitable for use, e.g., in the flameproofing of plastics.

We have now found that the flameproofing efficiency of the products described in German published specification Offenlegungsschrift No. 2,315,493 can be considerably improved by using the phosphorus-containing sulfamide derivatives of the present invention as flameproofing agents.

The present invention relates more particularly to phosphorus-containing sulfamide derivatives of the general formula (I)

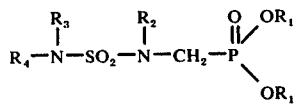

in which $R_1$ stands for an alkyl radical having from 1 to 6 carbon atoms and being halogen-substituted, if desired or stands for an aryl radical, and $R_2$, $R_3$ and $R_4$, being identical or different each stand for a hydrogen atom, a hydroxyalkyl group or a radical of the formula:

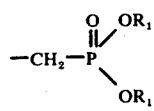

The phosphorus-containing sulfamide derivatives of general formula (I) preferably comprise the following compounds of formulae (a) – (n):

a) $H_2N-SO_2-NH-CH_2-\overset{\overset{O}{\|}}{P}-(OCH_2CH_3)_2$ b) $H_2N-SO_2-\underset{\underset{CH_2OH}{|}}{N}-CH_2-\overset{\overset{O}{\|}}{P}-(OCH_2CH_3)_2$ c) $(HOCH_2)_2-N-SO_2-\underset{\underset{CH_2OH}{|}}{N}-CH_2-\overset{\overset{O}{\|}}{P}-(OCH_2CH_3)_2$ d) $(CH_3O)_2-\overset{\overset{O}{\|}}{P}-CH_2-\underset{\underset{H}{|}}{N}-SO_2-\underset{\underset{H}{|}}{N}-CH_2-\overset{\overset{O}{\|}}{P}-(OCH_3)_2$ e) $(CH_3CH_2O)_2-\overset{\overset{O}{\|}}{P}-CH_2-\underset{\underset{H}{|}}{N}-SO_2-\underset{\underset{H}{|}}{N}-CH_2-\overset{\overset{O}{\|}}{P}-(OCH_2CH_3)_2$ f) $(ClCH_2CH_2O)_2-\overset{\overset{O}{\|}}{P}-CH_2-\underset{\underset{H}{|}}{N}-$

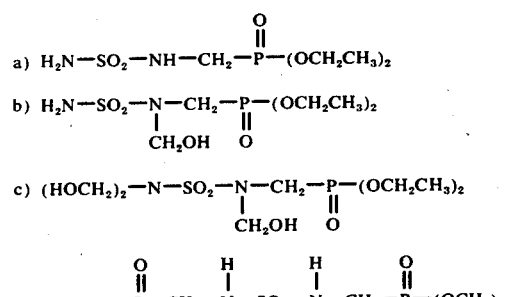

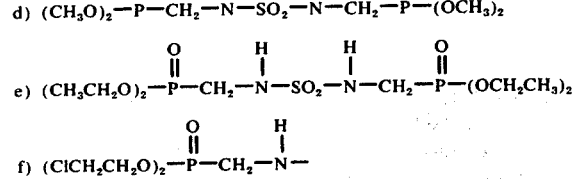

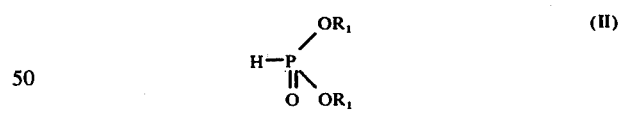

The compounds of the present invention are generally obtained in the form of colorless, highly viscous and undistillable liquids.

The present invention also relates to a process for making the phosphorus-containing sulfamide derivatives of general formula (I), which comprises reacting a sulfamide with formaldehyde and a dialkyl or diarylphosphite of general formula (II)

$$H-\underset{\underset{O}{\|}}{P}\overset{OR_1}{\underset{OR_1}{\diagdown}}  \qquad (II)$$

in which $R_1$ stands for an alkyl radical having from 1 to 6 carbon atoms and being halogenated, if desired, or stands for an aryl radical, in stoechiometric proportions, in the presence of a basic catalyst and, if desired, in the further presence of a solvent or diluent, at temperatures within the range about 10° and 80° C, at a pH-value within the range about 7 and 12 and for a period within the range about 1 and 3 hours, and distilling the resulting reaction mixture so as to remove reaction water and solvent or diluent, if any, therefrom.

The formaldehyde reactant in the present process may be used in gas form or in the form of a solution, e.g., in the form of 30–38 weight % aqueous formalin solutions, or in the form of substances yielding formaldehyde, such as paraformaldehyde or trioxane. The further reaction parameters, such as catalyst, reaction temperature or solvent or diluent, are more or less a function of the particular form in which the formaldehyde is used. In those cases in which an about 30-38 weight % formalin solution is used, it has been found advantageous to use sodium hydroxide, preferably in the form of an about 20-40 weight % aqueous solution, as the catalyst, without any need to add a further solvent or diluent. In this event, the reaction is effected at temperatures within the range about 15° and 25° C. On the other hand, in those cases in which free formaldehyde or chemically combined formaldehyde, e.g., in the form of paraformaldehyde or trioxane, is used, it is advantageous for the reaction to be effected in the presence of an organic solvent or diluent, such as low molecular aliphatic alcohols, linear or cyclic ethers, benzene or toluene. In this connection, it is good practice to effect the reaction in the presence of a catalyst, which preferably is a sodium alcoholate of a low molecular aliphatic alcohol, at preferred temperatures within the range about 40° and 60° C. With respect to the alcoholate solution, it is advantageous for it to contain between 0.01 and 0.1 gram atoms of sodium.

The process of the present invention may be effected, for example, in the following manner: The starting materials, such as sulfamide, formaldehyde and the compound of general formula (II) are mixed together and caused to react by adding the basic catalyst thereto, if desired in the presence of a solvent or diluent, the reaction taking place at temperatures within the range 10° and 80° C. It is also possible, however, for the starting materials to be added to the catalyst solution. It is more preferable, however, to charge a reactor with sulfamide and formaldehyde, if desired in the presence of the solvent or diluent, add the basic catalyst thereto so as to establish a preferred pH-value within the range 8 and 9, and then to add the compound of formula (II), while the pH-value is kept constant. The reaction mixture is allowed to react for a period within the range 1 and 3 hours at temperatures within the range 10° and 80° C and volatile constituents, such was water or solvent or diluent, are distilled off.

In carrying out the process of the present invention, it has also been found advantageous to use the individual starting materials in the theoretically necessary molar ratios. In other words, it is possible for 1 mol of formaldehyde and 1 mol of the compound of formula (II) to be used per hydrogen atom of the sulfamide, however, without the need to react all of the reactive hydrogen atoms of the sulfamide with formaldehyde and the formula (II) compound. The invention thus provides for the use of the sulfamide, formaldehyde and formula (II) compound reactants in a molar ratio within the range 1:1:1 (lower limit) and 1:4:4 (upper limit).

The products of the present invention have gained commercial interest as reactive and highly efficient agents rendering combustible substances, especially polyurethane foam plastics, flameproof. As regards their efficiency, they have been found to compare very favorably with compounds having a similar constitution, such as N-dimethylphosphonomethyl-p-toluene sulfamide of the following formula:

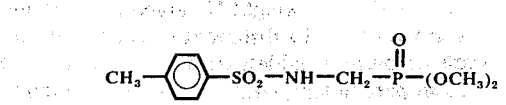

described in German published specification Offenlegungsschrift 2,315,493, Example 1.

The following Examples illustrate the invention without limiting it thereto.

EXAMPLE 1

The compound of the following formula was made:

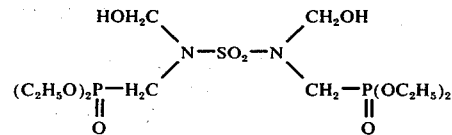

To this end, 24 g (0.25 mol) of sulfamide and 30 g (1 mol) of paraformaldehyde were suspended at room temperature in 150 cc of dioxane and a pH-value of 8 was established in the suspension by adding sodium ethylate thereto. Following this, 69 g (0.5 mol) of diethylphosphite was added. The temperature of the suspension increased to about 50° C and a clear solution was obtained. After a post-reaction period of 1 hour, the solution was heated to about 50° C so as to evaporate volatile constituents. 112 g of N,N'-bis-(hydroxymethyl)-N,N'-bis-(diethylphosphonomethyl)-sulfamide was obtained as A colorless viscous liquid. The yield was 98.5% of the theoretical. The product so obtained was analyzed and the following results were obtained:

|  | P | N | S | OH |
|---|---|---|---|---|
| Calculated: | 13.58 % | 6.14 % | 7.02 % | 7.45 % |
| Found: | 13.30 % | 6.13 % | 7.40 % | 7.88 % |

EXAMPLE 2

A mixture was prepared from 24 g (0.25 mol) of sulfamide and 79 g (1 mol) of 38% formalin and a pH-value of 8 was established therein by adding a 20 weight % sodium hydroxide solution thereto. 69 g (0.5 mol) of diethylphosphite was added at 25° C. After a reaction period of 2 hours, the reaction mixture was distilled and freed from the water contained therein. The resulting product was subjected to NMR-spectroscopy and to elementary analysis and found to be identical with the product obtained in Example 1.

EXAMPLES 3-5

The procedure was the same as that described in Example 1 save that dibutyl phosphite, dihexyl phosphite and diphenyl phosphite, respectively, were used as the phosphite component. The resulting final product was identified by NMR-spectroscopy and elementary analysis.

EXAMPLE 6

The compound of the following formula was made.

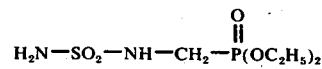

To this end, 48 g (0.5 mol) of sulfamide and 15 g (0.5 mol) of paraformaldehyde were dissolved at 50° C in 100 cc of dioxane. Sodium ethylate was added to the reaction batch to establish a pH-value of 8 and 69 g (0.5 mol) of diethyl phosphite was added at room temperature. The solvent was distilled off and an oily product remained behind. It was subjected to ¹H-NMR-spectroscopy and found to have the formula indicated above.

EXAMPLE 7

The compound of the following formula was made.

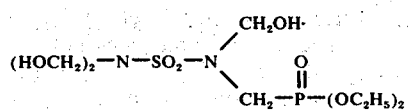

As described in Example 6, 20 g (0.5 mol) of sulfamide was reacted with 30 g (1 mol) of paraformaldehyde and 34.5 g (0.25 mol) of diethylphosphite. The product was subjected to ¹H-NMR-spectroscopy and found to be identical with the product having the above formula.

EXAMPLE 8

The compound of the following formula was made:

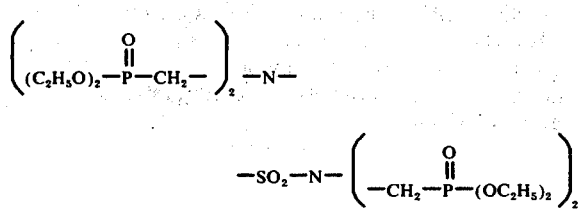

As described in Example 1, 24 g (0.25 mol) of sulfamide was reacted with 30 g (1 mol) of paraformaldehyde and 138 g (1 mol) of diethyl phosphite. The solvent was distilled off and an oil was obtained. It was subjected to ¹H-NMR-spectroscopy and found to be identical with the compound having the above formula.

EXAMPLE 9

The flameproofing efficiency of the products of the present invention was identified and compared with that of known flameproofing agents.

To test the flameproofing efficiency of the present products, they were incorporated with polyurethane soft foams. The polyurethane soft foams were made as follows:

The quantities of flameproofing agents specified in the Table hereinafter were blended together at room temperature with the following materials:

- 100g of a partially branched polyetherpolyol based on propylene oxide having a hydroxyl number of 46 mg KOH/g, a molecular weight of 3 500, a viscosity of 575 centipoises at 25° C and containing primary and secondary OH-groups in the ratio of 22:78 (Desmophen 3800, a product of Bayer AG, Leverkusen)
- 4.2g of water
- 0.12g of triethylene diamine
- 0.2g of tin(II)octoate
- 1.0g of a polyethylene polydimethylsiloxane block copolymer having a viscosity of 1200 centistokes at 25° C and a unit weight of 1.03 (L 540, a product of Union Carbide).

The blend was admixed with rapid agitation with 55.2 g of toluylene diisocyanate (a 20:80 blend of the 2,4 and 2,6-isomers). After about 20 seconds, the mixture began foaming. It was poured in a container. After a certain expansion period, the foam commenced hardening. It was hard after 15 minutes.

The foams so made were tested as to their combustibility (No. 302, Motor Vehicle Safety Standard of the Federal Highway Administration, USA). To this end, specimens with the dimensions of 100 × 360 mm and with a thickness of at most 13 mm were placed in a test chamber, held in horizontal position and contacted for 15 seconds with a flame 35 mm long. The propagation rate of the flame front was identified. The results obtained are indicated in the following Table.

TABLE

| Flameproofing agents | I | II | III | |
|---|---|---|---|---|
| A | 12 | 100 | SE/B | 76 mm |
|   | 18 | 80  | SE/NBR | 22 mm |
| B | 12 | 95  | B | 61 mm/min |
|   | 18 |     | SE/B | 59 mm |

In the above Table, the following terms have the following meanings:

Flameproofing agent A: a product of Example 1

Flameproofing agent B: N-dimethylphosphonomethyl-p-toluene-sulfamide (the product described in Example 1 of German published specification Offenlegungsschrift No. 2,345,493)

Column I: Parts by weight of flameproofing agent per 100 parts by weight of partially branched polyether polyol (Desmophen 3800, Bayer AG, Leverkusen)

Column II: Expansion period of polyurethane foam

Column III:

SE/B:

Flame extinguished within total area determined by metering points; the burn-up length was more than 38 mm, from start-up of test Column III:

SE/NBR:

Material extinguished within 60 seconds from start-up of test; burn-up length was less than 38 mm, from start up of test B: Flame spread out over entire testing area within time indicated.

As can be seen, the foams rendered flameproof with the agents A of the present invention compare favorably in their burn-up behavior with those rendered flameproof by means of known flameproofing agent B. In other words, the flameproofing agents of the present invention provide technically beneficial effects.

I claim:

1. A process for making phosphorus-containing sulfamide derivatives of the general formula (I)

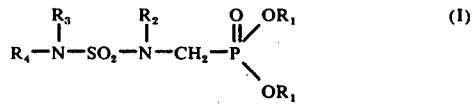

in which $R_1$ stands for an alkyl radical or a halogenated alkyl radical having from 1 to 6 carbon atoms or an aryl radical, and $R_2$, $R_3$ and $R_4$, being identical or different, each stand for a hydrogen atom, a hydroxyalkyl group or a radical of the formula:

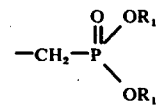

which process comprises reacting a sulfamide with formaldehyde and a dialkyl or diarylphosphite of general formula (II)

in which $R_1$ stands for an alkyl radical or a halogenated alkyl radical having from 1 to 6 carbon atoms, or stands for an aryl radical, in stoichiometric proportions, in the presence of a basic catalyst and, if desired, in the further presence of a solvent or diluent, at temperatures within the range about 10° and 80° C, at a pH-value within the range about 7 and 12 and for a period within the range 1 and 3 hours, and distilling the resulting reaction mixture so as to remove reaction water and solvent or diluent, if any, therefrom.

2. The process as claimed in claim 1, wherein the formaldehyde is used in free form or in the form of an aqueous about 30–38 weight % solution, or in the form of paraformaldehyde or trioxane.

3. The process as claimed in claim 1, wherein the substituent $R_1$ stands for a phenyl radical.

4. The process as claimed in claim 1, wherein the basic catalyst is sodium hydroxide or a sodium alcoholate.

5. The process as claimed in claim 1, wherein the formaldehyde is used in the form of an aqueous 30–38 weight % formalin solution, the catalyst is an about 20–40 weight % sodium hydroxide solution and the reaction is effected at temperatures within the range about 15° and 25° C.

6. The process as claimed in claim 1, wherein the solvent or diluent is a low molecular aliphatic alcohol, a linear or cyclic ether or benzene or toluene.

7. The process as claimed in claim 1, wherein the formaldehyde is used in the form of anhydrous material together with an organic solvent or diluent, the catalyst is a sodium alcoholate solution of low molecular aliphatic alcohols, and the reaction is effected at temperatures within the range about 40° and 60° C.

8. The process as claimed in claim 1, wherein the sodium alcoholate solution contains between about 0.01 and 0.1 gram atom of sodium.

9. The process as claimed in claim 1, wherein a basic catalyst is added to the blend of starting materials to establish a pH-value within the range 8 and 9 therein.

10. The process as claimed in claim 6, wherein the low molecular aliphatic alcohol is methanol or ethanol and the linear or cyclic ether is diethylester, dioxane or tetrahydrofurane.

* * * * *